United States Patent
Goker-Alpan et al.

(10) Patent No.: US 12,364,673 B2
(45) Date of Patent: Jul. 22, 2025

(54) METHODS AND COMPOSITIONS FOR TREATING LYSOSOMAL STORAGE DISORDERS: AMBROXOL AS TREATMENT AGENT FOR MUCOPOLYSACCHARIDOSES III (SANFILIPPO SYNDROME)

(71) Applicants: Lysosomal and Rare Disorders Research and Treatment Center, Inc., Fairfax, VA (US); Rare Cures Corporation, Saratoga Springs, NY (US)

(72) Inventors: Ozlem Goker-Alpan, Fairfax, VA (US); Margarita M. Ivanova, Fairfax, VA (US)

(73) Assignees: Lysosomal and Rare Disorders Research and Treatment Center, Inc., Fairfax, VA (US); Rare Cures Corporation, Saratoga Springs, NY (US)

( * ) Notice: Subject to any disclaimer, the term of this patent is extended or adjusted under 35 U.S.C. 154(b) by 779 days.

(21) Appl. No.: 17/431,336

(22) PCT Filed: Feb. 14, 2020

(86) PCT No.: PCT/US2020/018435
§ 371 (c)(1),
(2) Date: Aug. 16, 2021

(87) PCT Pub. No.: WO2020/168294
PCT Pub. Date: Aug. 20, 2020

(65) Prior Publication Data
US 2022/0133653 A1    May 5, 2022

Related U.S. Application Data

(60) Provisional application No. 62/806,437, filed on Feb. 15, 2019.

(51) Int. Cl.
*A61K 31/137* (2006.01)
*A61P 3/00* (2006.01)

(52) U.S. Cl.
CPC .............. *A61K 31/137* (2013.01); *A61P 3/00* (2018.01)

(58) Field of Classification Search
None
See application file for complete search history.

(56) References Cited

U.S. PATENT DOCUMENTS

| | | |
|---|---|---|
| 2010/0196279 A1 | 8/2010 | Lockhart |
| 2011/0286993 A1 | 11/2011 | Jensen et al. |
| 2015/0258081 A1* | 9/2015 | Lukas .................. A61K 31/137 514/315 |
| 2016/0068580 A1 | 3/2016 | Cho et al. |
| 2019/0060289 A1 | 2/2019 | Deretic et al. |
| 2020/0339535 A1 | 10/2020 | Romero et al. |
| 2023/0404972 A1 | 12/2023 | Limgala et al. |

FOREIGN PATENT DOCUMENTS

| | | |
|---|---|---|
| WO | 1999047545 A2 | 9/1999 |
| WO | 2013/091897 A1 | 6/2013 |
| WO | 2020168294 A1 | 8/2020 |
| WO | 2020210798 A1 | 10/2020 |

OTHER PUBLICATIONS

International Search Report issued in PCT/US2020/018435; mailed Jun. 18, 2020.
IPRP and Written Opinion issued in PCT/US2020/018435; issued Aug. 10, 2021.
Hennermann J. B.; Development of new therapies for rare diseases, Monatsschrift Fuer Kinderheilkunde, Springer Verlag, DE, vol. 165, No. 3, Jan. 19, 2017 (Jan. 19, 2017), pp. 226-233.
Magalhaes, J., Gegg, M. E., Migdalska-Richards, A., and Schapira, A. H. (2018) Effects of ambroxol on the autophagy-lysosome pathway and mitochondria in primary cortical neurons. Scientific reports 8, 1385.
Aflaki et al. "Lysosomal storage and impaired autophagy lead to inflammasome activation in Gaucher macrophages" Aging Cell; Feb. 2016; vol. 15, No. 1, pp. 77-88.
Burkovetskaya et al. "Caspase 1 activity influences juvenile Batten disease (CLN3) pathogenesis" Journal of Neurochemistry; Mar. 2019; vol. 148, No. 5, pp. 652-668.
Darios & Stevanin "Impairment of lysosome function and autophagy in rare neurodegenerative diseases" Journal of Molecular Biology; Apr. 2020; vol. 432, No. 8, pp. 2717-2734.
Lieberman et al. "Autophagy in lysosomal storage disorders" Autophagy; May 2012; vol. 8, No. 5, pp. 719-730.
Limgala et al. "Time of initiating enzyme replacement therapy Affects immune abnormalities and disease severity in patients with Gaucher disease" PLoS One; Dec. 2016; vol. 11, No. 12, art. e0168135, doi: 10.1371/journal.pone.0168135, 16 pages.
Limgala et al. "Altered immune phenotypes in subjects with Fabry disease and responses to switching from agalsidase alfa to agalsidase beta" American Journal of Translational Research; Mar. 2019; vol. 11, No. 3, pp. 1683-1696.
Lorincz & Juhasz "Autophagosome-lysosome fusion" Journal of Molecular Biology; Apr. 2020; vol. 432, No. 8, pp. 2462-2482.
Parenti et al. "Pharmacological chaperone therapy: Preclinical development, clinical translation, and prospects for the treatment of lysosomal storage disorders" Molecular Therapy; May 2015; vol. 23, No. 7, pp. 1138-1148.
Persaud-Sawin et al. "Cell death pathways in juvenile Batten disease" Apoptosis; Oct. 2005; vol. 10, No. 5, pp. 973-985.

(Continued)

*Primary Examiner* — Bong-Sook Baek
(74) *Attorney, Agent, or Firm* — Studebaker Brackett PLLC

(57) ABSTRACT

Methods for treating MPS III diseases are disclosed. The methods involve administering a therapeutically effective amount of a composition comprising ambroxol to a subject with the disease. Also disclosed are pharmaceuticals suitable for treating MPS III diseases.

16 Claims, 10 Drawing Sheets

(56) References Cited

OTHER PUBLICATIONS

Figure 1:
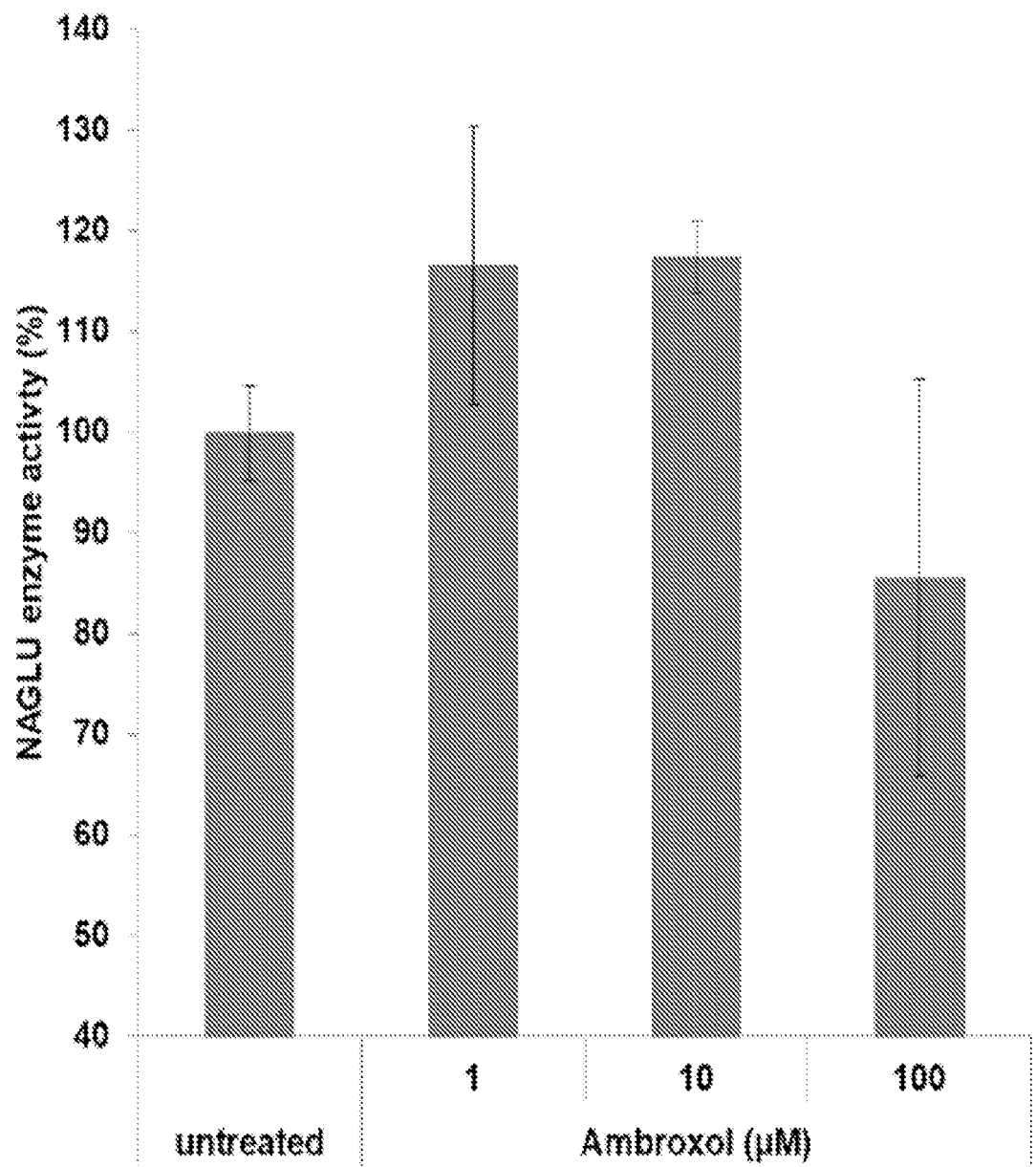

Rigante et al. "Overview of immune abnormalities in lysosomal storage disorders" Immunology Letters; Aug. 2017; vol. 188, pp. 79-85.
Rozenfeld & Feriozzi "Contribution of inflammatory pathways to Fabry disease pathogenesis" Molecular Genetics and Metabolism; Nov. 2017; vol. 122, No. 3, pp. 19-27.
Saffari et al. "Linking mitochondrial dysfunction to neurodegeneration in lysosomal storage diseases" Journal of Inherited Metabolic Disease; Sep. 2017; vol. 40, No. 5, pp. 631-640.
Son et al. "A novel human model of the neurodegenerative disease GM1 gangliosidosis using induced pluripotent stem cells demonstrates inflammasome activation" Journal of Pathology; Sep. 2015; vol. 237, No. 1, pp. 98-110.
Takamura et al. "Enhanced autophagy and mitochondrial aberrations in murine GM1-gangliosidosis" Biochemical and Biophysical Research Communications; Mar. 2008; vol. 367, No. 3, pp. 616-622.
Uribe-Carretero et al. "Lysosomal dysfunction: Connecting the dots in the landscape of human diseases" Biology; Jan. 2024; vol. 13, No. 1, art. 34, doi: 10.3390/biology13010034, 34 pages.
Yim & Mizushima "Lysosome biology in autophagy" Cell Discovery; Feb. 2020; vol. 6, art. 6, doi: 10.1038/s41421-020-0141-7, 12 pages.

\* cited by examiner

METHODS AND COMPOSITIONS FOR TREATING LYSOSOMAL STORAGE DISORDERS: AMBROXOL AS TREATMENT AGENT FOR MUCOPOLYSACCHARIDOSES III (SANFILIPPO SYNDROME)

PRIORITY

This application is the national phase application of and claims priority to International Application No. PCT/US2020/018435 filed on Feb. 14, 2020. International Application No. PCT/US2020/018435 claims the benefit of priority to United States Provisional Patent Application No. 62/806,437 entitled "Ambroxol as Treatment Agent for Mucopolysaccharidoses III (Sanfilippo Syndrome)" and filed Feb. 15, 2019. All patents, patent applications and publications mentioned in this disclosure are hereby incorporated by reference in their entirety as if each individual publication was specifically and individually indicated to be incorporated by reference.

BACKGROUND

Lysosomal Storage Diseases (LSDs) are a heterogeneous group of rare disorders, each of which is caused by the deficiency of a lysosomal enzyme or an essential cofactor leading to deposition of the substrate within the lysosomes, resulting in cellular, tissue dysfunction and organ dysfunction. While clinical features vary from disease to disease, neurological involvement is quite common and may include developmental delay, behavioral/psychiatric disturbances, mental deterioration, seizures, and regression. Furthermore, it is recently shown that the genetic carriers of certain lysosomal disorders or individuals with a heterozygote mutation in a gene encoding for a Lysosomal protein, while may not develop the characteristic disease manifestations, but may be prone to develop an adult onset neurodegenerative disorder such as Parkinson disease or Alzheimer disease (ref: https://world wide web.ncbi.nlm.nih.gov/pubmed/18852351: Arch Neurol. 2008 October; 65(10):1353-7. doi: 10.1001/archneur.65.10.1353. The spectrum of parkinsonian manifestations associated with glucocerebrosidase mutations. Goker-Alpan O, Lopez G, Vithayathil J, Davis J, Hallett M, Sidransky E.)

Mucopolysaccharidosis type III (MPS III), also known as Sanfilippo Syndrome, is a lysosomal storage disease caused by a congenital deficiency in one of the four enzymes that degrades heparan sulfate (HS). HS is a glycosaminoglycan (GAG) that is a product of the breakdown of proteoglycans which are constituents of the extracellular matrix. The prime manifestation of Sanflippo syndrome is progressive neurodegeneration. Harris described the disorder in 1961: a girl having hepatosplenomegaly, with normal skeletal structure and excreted large quantities of a single GAG, namely HS. The disorder was named after Sylvester Sanfilippo who in 1963 reported patients with mucopolysaccharides in the urine and severe neurological dysfunction manifesting in loss of learned abilities and behavioral problems.

SUMMARY

One embodiment is directed to a method of treating a MPS III disease in a subject, comprising the step of administering a therapeutically effective amount of a composition comprising ambroxol or a salt thereof or a hydrochloride thereof to the subject.

The phrase "in any aspect of this disclosure" refers to at least "in any aspect of the methods, compositions, and pharmaceutical compositions of this disclosure."

In any aspect of this disclosure, the MPS III disease may be at least one selected from the group consisting of: MPS III Type A, MPS III Type B, MPS III Type C, and MPS III Type D. Recently, MPS III Type E, which is discussed in more detail below, has also been proposed. Therefore, MPS III disease that may be treated by the methods of this disclosure can be at least one selected from the group consisting of MPS III Type A, MPS III Type B, MPS III Type C, MPS III Type D, and MPS III Type E.

In any aspect of this disclosure, administering is at least one selected from the group consisting of: administering orally, administering transmucosally, administering sublingually, administering buccally, administering intranasally, administering transurethrally, administering rectally, administering topically, administering transdermally, administering parenterally, and administering intrathecally.

In another aspect, the methods, compositions, and pharmaceutical compositions of this disclosure has the benefit of increasing the enzymatic activity of N-acetyl-alpha-glucosaminidase (NAGLU) in the subject. In any aspect of this disclosure, the subject may have a mutation in a gene encoding NAGLU. The subject may be homozygous for a mutated NAGLU gene—that is, the subject may have two copied of the mutated NAGLU gene and no copy of a normal (also called wildtype) NAGLU gene. The subject may have a NAGLU enzyme with reduced activity and have MPS III Type B disease.

In a preferred aspect, the subject (1) has a mutation in a gene encoding N-acetyl-alpha-glucosaminidase (NAGLU), (2) the subject is homozygous for the mutated NAGLU gene meaning the subject has two copies of the mutated NAGLU gene and no copy of a normal (also called wildtype) NAGLU gene, (3) the subject have a mutated NAGLU enzyme with reduced activity, and (4) the methods, compositions, or pharmaceutical compositions of this disclosure compensate for the mutated NAGLU enzyme by increasing the enzymatic activity of this mutated NAGLU enzyme in the subject.

In another aspect, the subject produces an enzyme which is "an N-acetyl-alpha-glucosaminidase enzyme with reduced activity" and the method and pharmaceutical compositions disclosed increase the enzymatic activity of the enzyme (N-acetyl-alpha-glucosaminidase enzyme with reduced activity).

In another aspect, the methods, compositions, or pharmaceutical compositions of this disclosure have the benefit of increasing the fusion rate of autophagic vesicles with lysosomes in the subject. The subject may be any subject described in this disclosure. For example, the subject may have one or more of the following: (1) have one or two copies (heterozygous or homozygous) of a mutated gene where the gene is the SGSH gene, the NAGLU gene, the HGSNAT gene, the GNS gene or a combination thereof. That is, while the subject may have a mutation (homozygous or heterozygous) in the SGSH gene, the NAGLU gene, the HGSNAT gene, the GNS gene or a combination thereof, the methods, compositions, or pharmaceutical compositions can treat these mutations by increasing the fusion rate of autophagic vesicles with lysosomes in the subject.

In another aspect, the methods, compositions, or pharmaceutical compositions of this disclosure has the benefit of decreasing heparin sulfate levels in the subject. For example, the heparin sulfate level is decreased in the cells or the urine of the subject. In another aspect, the methods, compositions, or pharmaceutical compositions of this disclosure has the benefit of increasing intracellular heparin sulfate degradation in the subject.

In another aspect, the methods, compositions, or pharmaceutical compositions of this disclosure has the benefit of not increasing heparan-alpha-glucosaminide N-acetyltransferase (HGSNAT) activity in the subject.

In any aspect of this disclosure, ambroxol may be selected from the group consisting of ambroxol, a salt of ambroxol (e.g., a hydrochloride salt of ambroxol (also called hydrochloride of ambroxol)).

In any aspect of this disclosure, the subject may have a mutation in at least one gene selected from the group consisting of: SGSH gene, NAGLU gene, HGSNAT gene, and GNS gene. In any aspect of this disclosure, the subject may be homozygous/heterozygous for one or more mutations in a gene selected from the group consisting of: SGSH gene, NAGLU gene, HGSNAT gene, and GNS gene.

In any aspect of this disclosure, the subject may have a mutation in each of two copies of one gene selected from the group consisting of SGSH gene, NAGLU gene, HGSNAT gene, and GNS gene. That is, the subject is homozygous for mutations in both copies of a gene selected from the group consisting of SGSH gene, NAGLU gene, HGSNAT gene, and GNS gene. The two copies of the gene may have the same mutation or different mutations.

In any aspect of this disclosure, the subject may have a reduced activity for at least one enzyme selected from the group consisting of: sulfamidase, alpha-N-acetylglucosaminidase, acetyl-CoA:alpha-glucosaminide N-acetyltransferase, N-acetylglucosamine-6-sulfatase, and arylsulfatase G.

In any aspect of this disclosure, the method may further comprise a step of diagnosing a MPS III disease in the subject before the administration step. Diagnosing may be, for example, detecting a reduced activity for at least one enzyme in the subject, wherein the enzyme is selected from the group consisting of: sulfamidase, alpha-N-acetylglucosaminidase, acetyl-CoA:alpha-glucosaminide N-acetyltransferase, N-acetylglucosamine-6-sulfatase, and arylsulfatase G.

Another embodiment of the disclosure is directed to a pharmaceutical composition for treating an MPS III disease in a subject, which comprises a therapeutically effective amount of ambroxol and one or more pharmaceutically acceptable excipients. The MPS III disease may be any MPS III disease discussed in this disclosure such as at least one selected from the group consisting of: MPS III Type A, MPS III Type B, MPS III Type C, MPS III Type D, and MPS III Type E. The subject may have one or more mutations in at least one gene or at least two genes selected from the group consisting of: SGSH gene, NAGLU gene, HGSNAT gene, and GNS gene. For example, the subject may be homozygous for one or more mutations in a gene selected from the group consisting of: SGSH gene, NAGLU gene, HGSNAT gene, and GNS gene. The subject may have a reduced activity for at least one enzyme selected from the group consisting of: sulfamidase, alpha-N-acetylglucosaminidase, acetyl-CoA:alpha-glucosaminide N-acetyltransferase, N-acetylglucosamine-6-sulfatase, and arylsulfatase G. In one aspect, the subject produces a N-acetyl-alpha-glucosaminidase with reduced activity and the method increases the activity of the N-acetyl-alpha-glucosaminidase.

FIGURES

FIG. 1 Shows N-acetyl-alpha-glucosaminidase (NAGLU) enzyme activity level in PBMC (peripheral blood mononuclear cell) derived from a patient with MPS III Type B disease. PBMC were cultured for 5 days with an increasing concentration of ambroxol. Results are presented as a percentage of the negative control (cells cultured in the absence of ambroxol).

Figure 2:
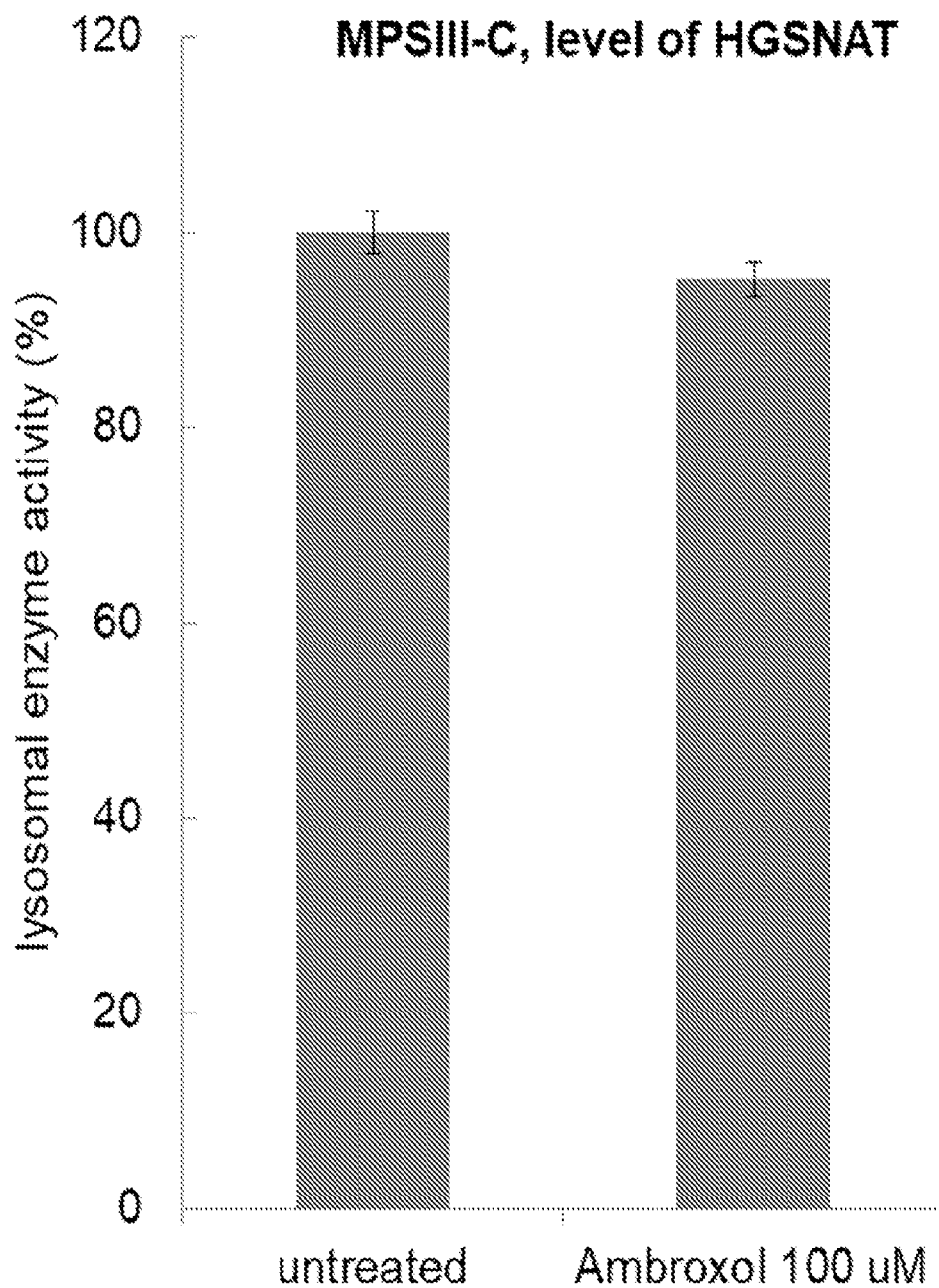

FIG. 2 Shows heparan-alpha-glucosaminide N-acetyltransferase (HGSNAT) enzyme activity level in PBMC derived from a patient with MPS III Type C disease. PBMC were cultured for 5 days with an increasing concentration of ambroxol. Results are presented as a percentage of the negative control (cells cultured in the absence of ambroxol).

Figure 3:
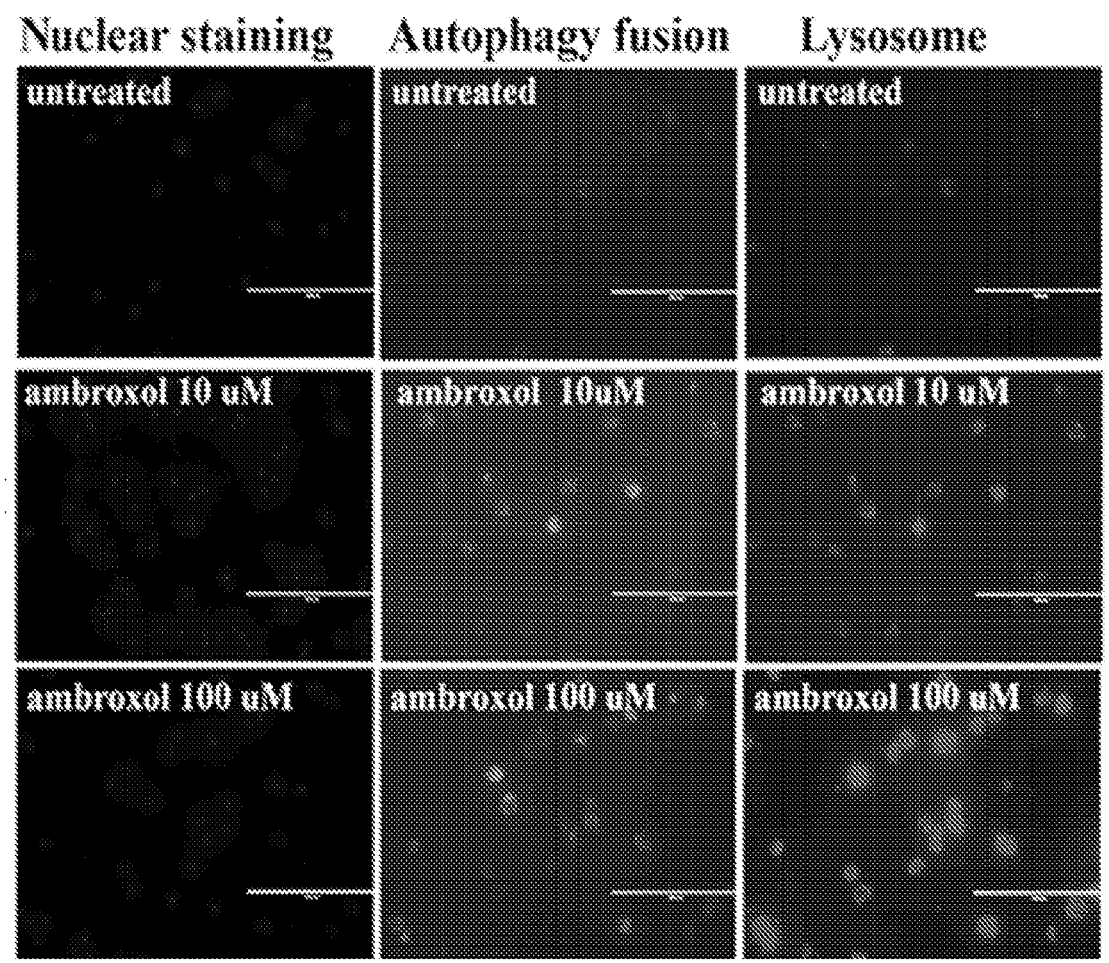

FIG. 3 Shows PBMC derived from a patient with MPS III Type B. Cells were incubated with increasing concentration of ambroxol for 5 days. Fluorescent imaging of autophagy fusion with the lysosome using DALGreen detection reagent (middle column which is originally in green color) and lysosome staining with LysoTracker dye (right column which is originally in red color). Fluorescent blue is nuclear staining (left column which is originally in blue color).

Figure 4:
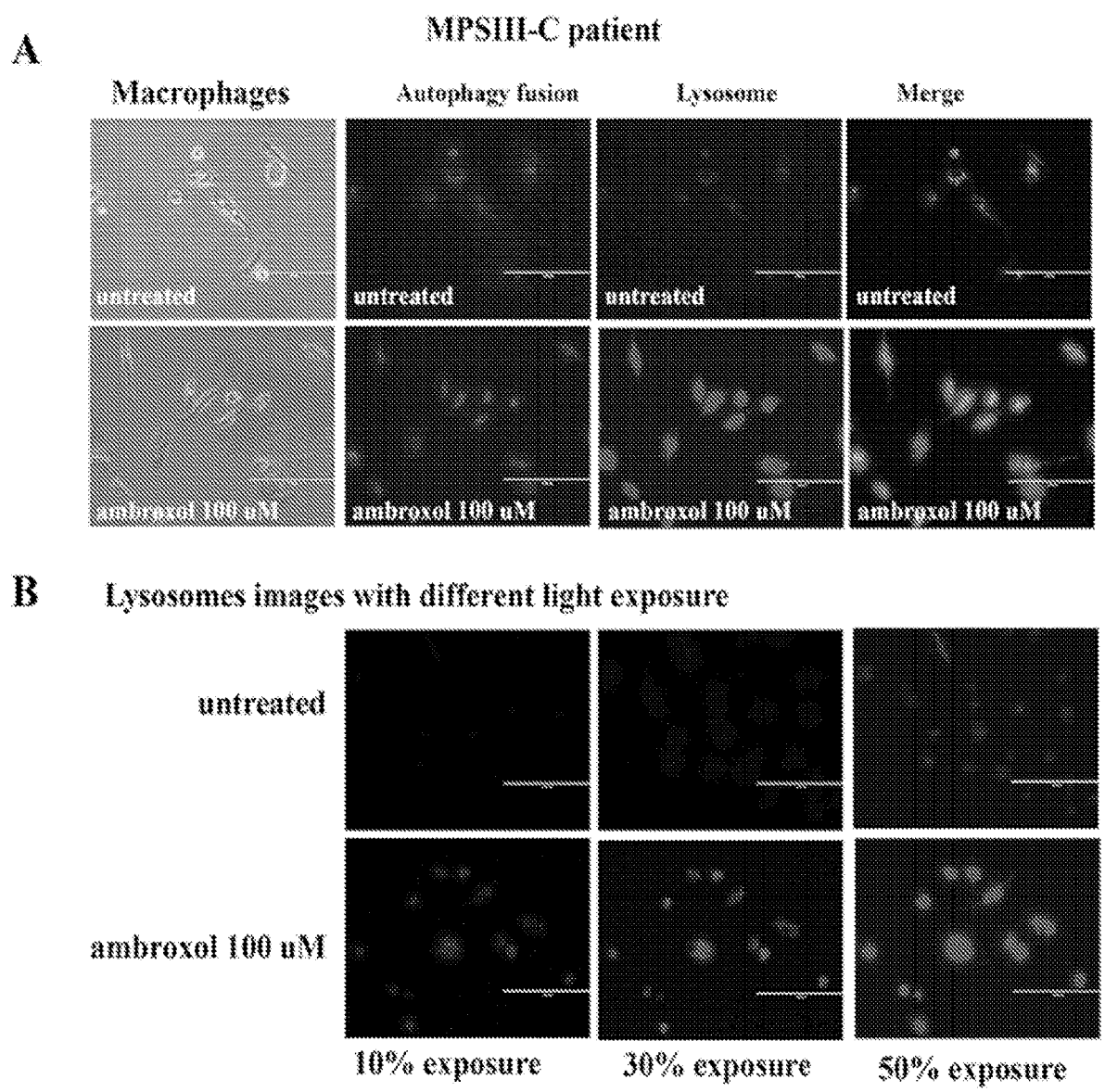

FIG. 4 Shows autophagy and lysosome staining in MPS III Type C macrophages. A. Fluorescent imaging of autophagy fusion with the lysosome using DALGreen detection reagent ($2^{nd}$ column from left which is originally in green color) and bright light images of macrophages (leftmost column which is originally in grey); lysosome staining with LysoTracker dye ($3^{rd}$ column from left which is originally in red color) and merged (rightmost or $4^{th}$ column from left). B. Increasing lysosomal mass in ambroxol incubated macrophages. Representative images after different time exposure showed the difference in fluorescence signal intensity.

Figure 5:
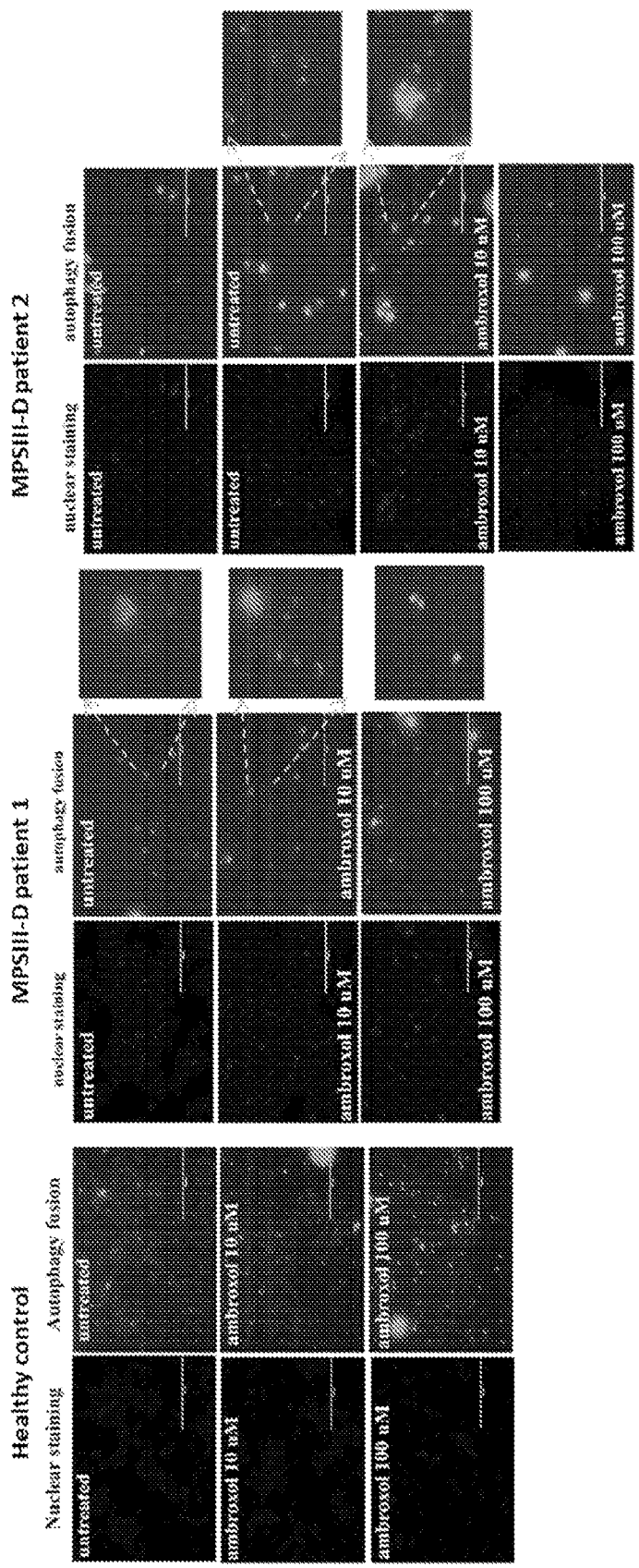

FIG. 5 Shows autophagy fusion staining in MPS III Type D.

The leftmost panel labeled "healthy control" has a left column originally in blue and a right column originally in green.

The middle panel labeled "MPSIII-D patient 1" has 3 columns: a left column originally in blue, a center and a right column originally in green.

The right panel labeled "MPSIII-D patient 2" has 3 columns: a left column originally in blue, a center and a right column originally in green. Panels originally in green are fluorescent imaging of autophagy fusion with the lysosome using DALGreen detection reagent (originally green color). Panels originally in blue are nuclear staining.

As stated above, the left side is PBMC for healthy control, the center is patient 1, the right panel is patient 2 with MPS III Type D. Arrows showing images with increasing magnification.

Figure 6:
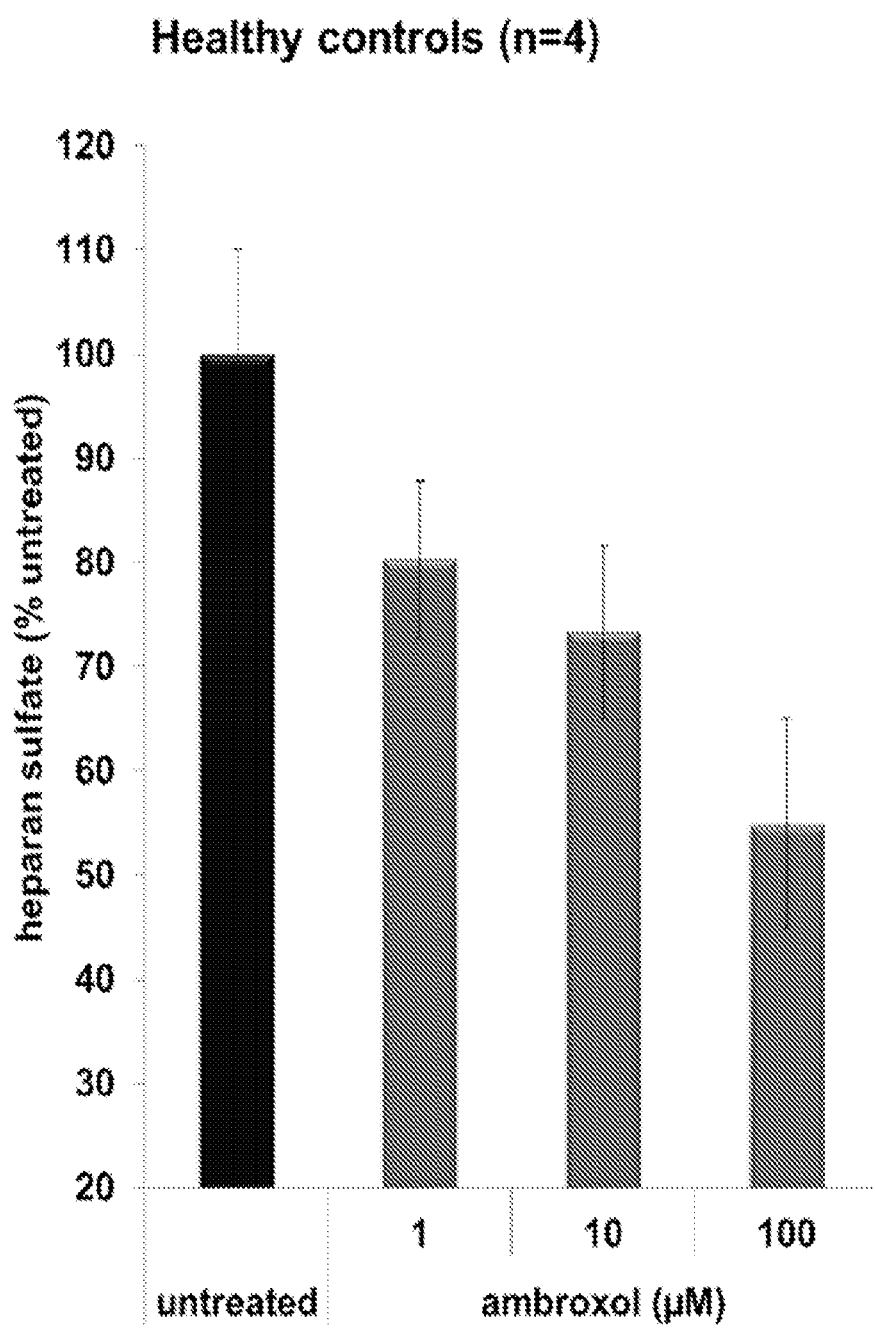

FIG. 6 Shows the heparan sulfate (HS) level in PBMC derived from healthy controls (n=4). PBMC were cultured for 5 days with an increasing concentration of ambroxol. Results are presented as a percentage of the negative control (cells cultured in the absence of ambroxol).

Figure 7:
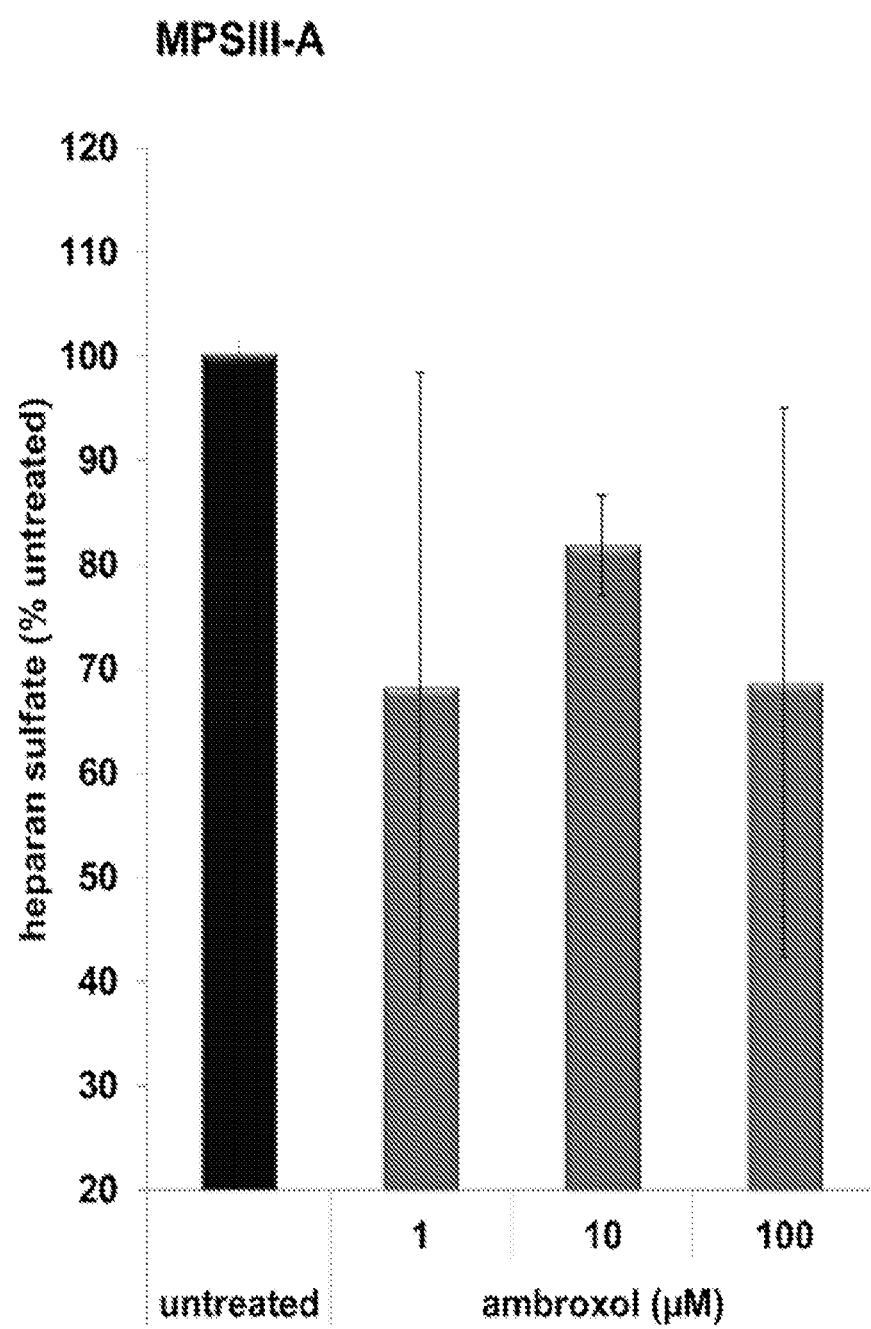

FIG. 7 Shows heparan sulfate (HS) level in PBMC derived from MPS III-A patient. PBMC were cultured for 5 days with an increasing concentration of ambroxol. Results are presented as a percentage of the negative control (cells cultured in the absence of ambroxol).

Figure 8:
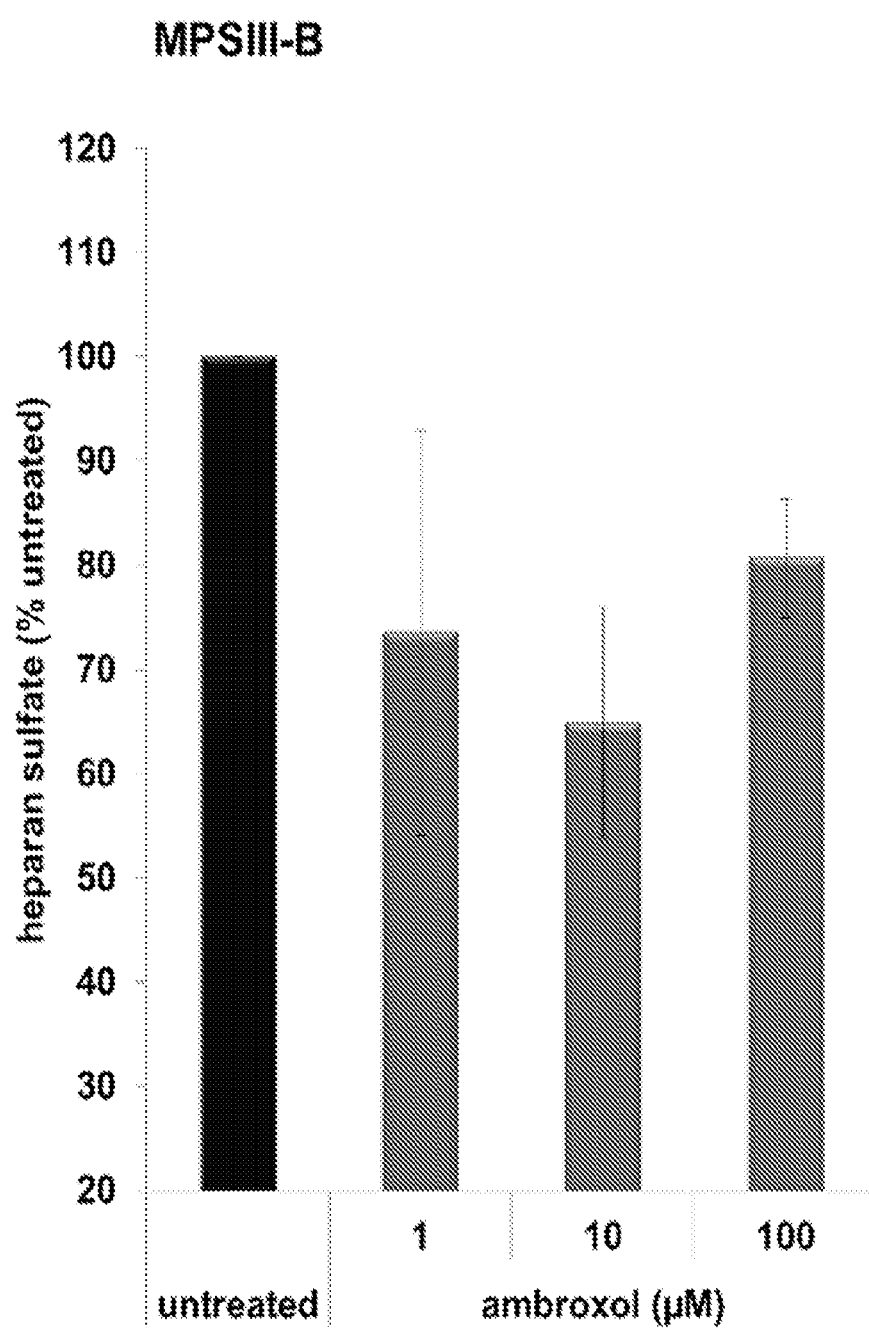

FIG. 8 Shows heparan sulfate (HS) level in PBMC derived from MPS III-B patient. PBMC were cultured for 5 days with an increasing concentration of ambroxol. Results are presented as a percentage of the negative control (cells cultured in the absence of ambroxol).

Figure 9:
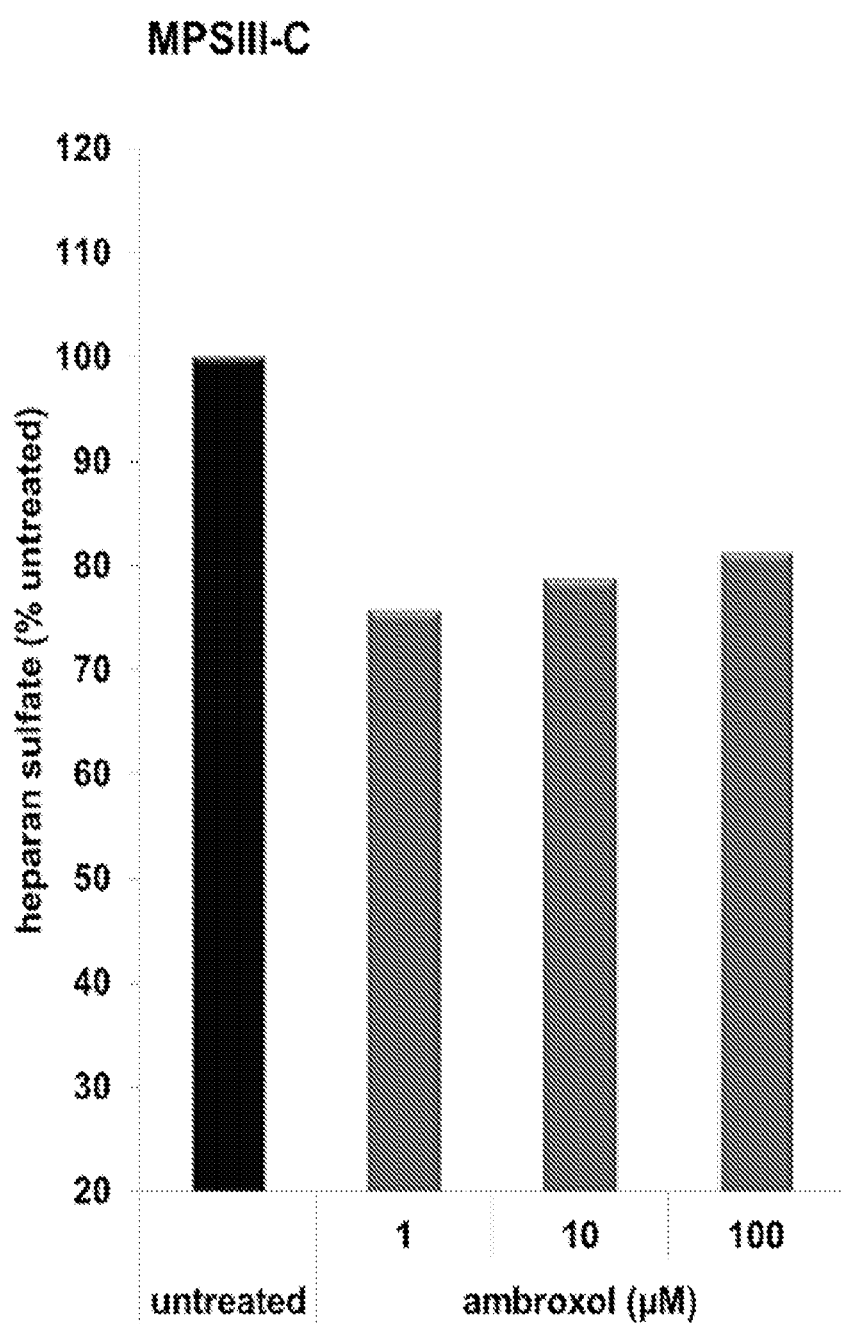

FIG. 9 Shows heparan sulfate (HS) level in PBMC derived from MPS III-C patient. PBMC were cultured for 5 days with an increasing concentration of ambroxol. Results are presented as a percentage of the negative control (cells cultured in the absence of ambroxol).

Figure 10:
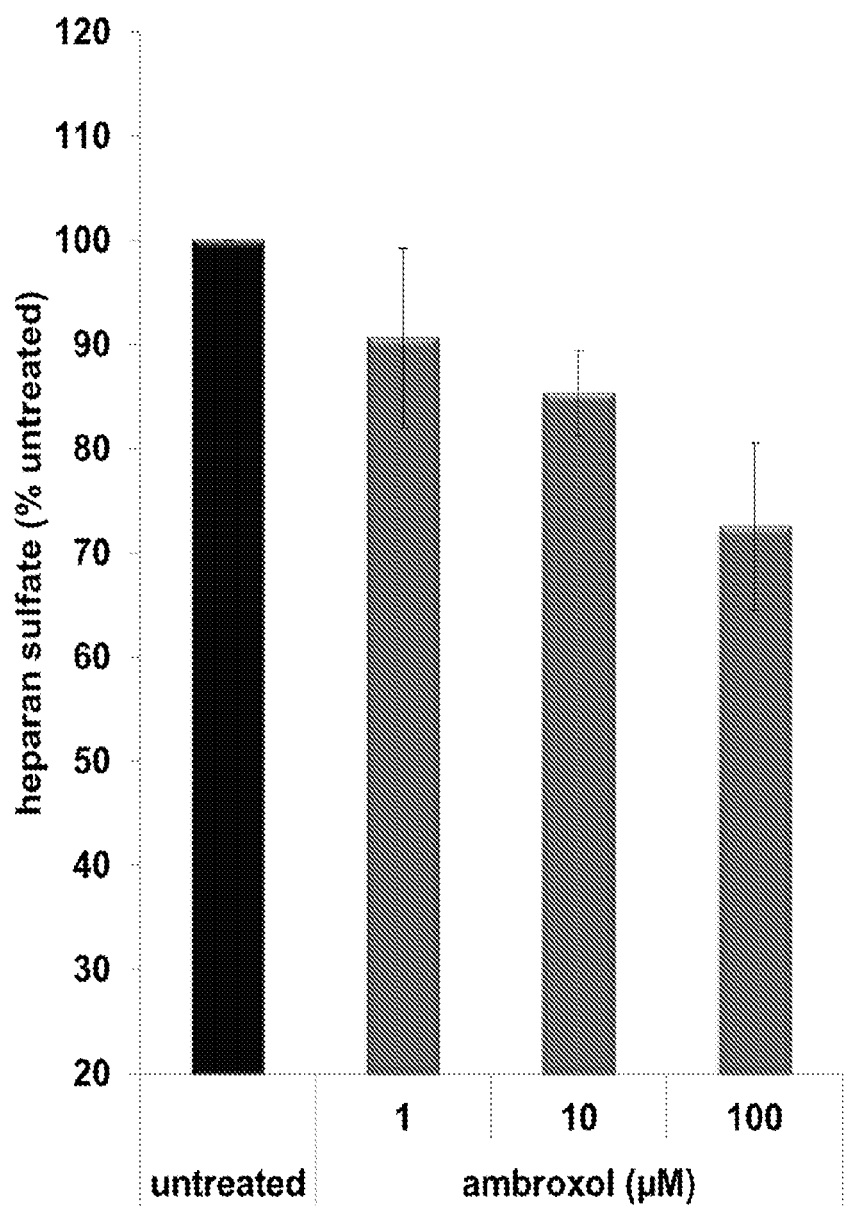

FIG. 10 Shows heparan sulfate (HS) level in PBMC derived from MPS III-D patient. PBMC were cultured for 5 days with an increasing concentration of ambroxol. Results are presented as a percentage of the negative control (cells cultured in the absence of ambroxol).

DETAILED DESCRIPTION

Ambroxol is the international generic name for trans-4-(2-Amino-3,5-dibromobenzylamino)-cyclohexanol. The most commonly used form is ambroxol's hydrochloride form. While this disclosure refers to ambroxol, it is understood that various forms of ambroxol are envisioned including salts thereof, solvates thereof, hydrates thereof, solid forms thereof, and including, for example, ambroxol hydrochloride—the most commonly used form.

Sanfilippo Syndrome, or mucopolysaccharidosis (MPS) type III, refers to one of five autosomal recessive, neurodegenerative lysosomal storage disorders due to the incomplete lysosomal degradation of heparan sulfate. The MPS III subtypes are caused by a deficiency in one of the enzymes involved in such degradations, and caused by a mutation in different genes. This can be summarized as follows:

Sanfilippo Syndrome, or mucopolysaccharidosis (MPS) type III, refers to one of five autosomal recessive, neurodegenerative lysosomal storage disorders due to the incomplete lysosomal degradation of heparan sulfate. The MPS III subtypes are caused by the deficiency of: sulfamidase (SGSH, MPS III-A); alpha-N-acetylglucosaminidase (NAGLU, MPS III-B); heparan acetyl CoA: alpha-glucosaminide N-acetyltransferase (HGSNAT, MPS III-C); N-acetylglucosamine 6-sulfatase (GNS, MPS III-D); or N-glucosamine 3-O-sulfatase (arylsulfatase G or ARSG, the currently putative MPS III-E). MPS III is considered the most common form of mucopolysaccharidoses with an estimated prevalence of 0.3-4.1/100,000 live births (1). This is summarized as follows.

| Sanfilippo Syndrome type or MPS-III type | Gene | Enzyme |
|---|---|---|
| Type A | SGSH | sulfamidase (also called heparan N-sulfatase, or N-sulfoglucosamine sulfohydrolase) |
| Type B | NAGLU | alpha-N-acetylglucosaminidase |
| Type C | HGSNAT | acetyl-CoA:alpha-glucosaminide N-acetyltransferase |
| Type D | GNS | N-acetylglucosamine-6-sulfatase |
| Type E | ARSG | arylsulfatase G |

The most common type of MPS III is Type A representing 60% of the cases. It is the result of mutations in the SGSH gene that lead to the deficiency of the enzyme heparan-N-sulfatase. Type B, which represents about 30% of patients, is caused by mutations in the NAGLU gene, resulting in the loss of N-acetyl-alpha-glucosaminidase enzyme activity. Types C and D are much less common, representing 10% of all cases, and are the result of the loss of activity of heparan acetyl CoA:alpha-glucosaminide N-acetyltransferase (caused by mutations in the HGSNAT gene) and N-acetylglucosamine-6-sulfatase (caused by mutations in the GNS gene), respectively. All four gene mutations result in progressive lysosomal accumulation of HS, increased plasma levels of HS, and increased excretion of HS or its fragments into body fluids.

MPS III patients have a deficiency in one or more enzymes involved in the breakdown of large sugar molecules—particularly heparan sulfate—called glycosaminoglycans (GAGs). GAG molecules are long unbranched polysaccharides containing a repeating disaccharide unit, which is composed of one modified sugar and one uronic acid. Since all four enzymes share the same pathway, each of their deficiencies causes the accumulation of the initial substrates, mostly HS. Heparan sulfate GAGs exist in the cell as proteoglycans that are catabolized within the lysosome. The degradative function of lysosomes relies on the capacity of the lysosomal membranes to associate with target membranes, such as those of autophagic vacuoles. Interfering with the composition of lysosomal membranes has been shown to affect trafficking and fusion within the lysosomal network. Lysosomal dysfunction may have wide-reaching consequences, such as the pathology of the mitochondrial system observed in the MPS III-C mouse, caused by the accumulation of dysfunctional mitochondria otherwise eliminated by normal autophagy and lysosomal function.

MPS III is generally characterized by significant central nervous system degeneration with relatively mild somatic involvement compared to other MPS syndromes. Symptoms usually begin between 1 to 4 years of age after normal or near-normal early development. Signs and symptoms include developmental delay (speech is generally much more delayed than motor development) and, severe behavioral problems, including hyperactivity and aggression. Enlargement of the liver and spleen are part of the clinical physical presentation. Frequent ear, nose, and throat infections, as well as hearing and visual impairment, also are common pathological presentations. The disease progress includes seizures, swallowing and feeding difficulties, continued loss of developmental skills, gait disturbance, and the onset of pyramidal signs eventually lead to a vegetative state and death at the end of the second or beginning of the third decade of life (1). Brain imaging shows significant cortical atrophy and ventriculomegaly due to loss of brain volume.

Besides physical symptoms, diagnosis by urinalysis can show elevated levels of heparan sulfate in the urine. In addition, all four types of Sanfilippo Syndrome show increased levels of GAGs in the urine. Additionally, urinary GAG levels are higher in infants and toddlers than in older children. The diagnosis may be confirmed by enzyme assay of skin fibroblasts or white blood cells. The enzyme assay is considered the most-credible diagnostic tool because it detects whether or not the enzymes in the cellular pathway breaking down heparan sulfate are present or not, providing a definitive answer. Another diagnostic tool can be gene sequencing.

It is commonly assumed that the four MPS III subtypes are clinically indistinguishable. However, some studies suggest that Type A is more severe, with an earlier onset, more rapid progression, and earlier death than the other types of MPS III (2). In general, symptoms and disease severity vary widely between patients, even between siblings with the same genotype (1).

To date, there is no established treatment for MPS III and care is symptomatic and supportive. Therapeutic approaches have included the use of small molecules including substrate reduction therapy, substrate optimization therapy, and chaperones. Hematopoietic stem cell transplant and bone marrow transplant have not been successful (3). Enzyme replacement therapy (ERT) has been approved for MPS I, II, and VI, but is currently being evaluated in clinical trials for MPS III as is gene therapy.

Ambroxol (or most used hydrochlorides thereof ambroxol hydrochloride) is an anti-inflammatory agent and a $Na^+$ channel blocker. It was developed for the treatment of airway mucus-hypersecretion and hyaline membrane disease in newborns. Ambroxol has a long history of treatment of acute and chronic bronchopulmonary diseases. In 2009, ambroxol was identified as a pharmacological chaperone for the lysosomal enzyme glucocerebrosidase (GCase) (4-6). Ambroxol has unique characteristics to assist in protein folding. It works with high activity at the preferred pH of the endoplasmic reticulum (ER) and lysosomal environments (5). At pH 4.3, near lysosomal pH, ambroxol does not inhibit the enzyme but instead becomes an activator of GCase. Additionally, ambroxol increased lysosomal integral membrane protein-2 (LIMP-2) which mediates GCase trafficking to lysosomes and activate saposin C (7, 8). Recent studies in a Gaucher disease-related Parkinson disease model indicate that ambroxol may help to reduce unwanted build-up of toxic proteins by activation of the autophagy-lysosomal pathway (9).

In this disclosure, we have surprisingly found that ambroxol can be used as a therapeutic agent to treat patients with MPS III. Our experiments and results are described in the Examples section.

The terms "treating" and "treatment" as used herein refer to relieving the symptoms or lessening the discomfort associated with MPS III disease.

By an "effective" amount or a "therapeutically effective amount" of a drug or pharmacologically active agent is meant a nontoxic but sufficient amount of the drug or agent to provide the desired effect, i.e., relieving the symptoms or lessening the discomfort associated with MPS III disease.

Administration

Ambroxol has several formulations and dosages available on the market, in the form of tablets, capsules oral solutions, syrups, injections, liquid solutions for aerosolization, etc. For adults and children over 12 years, the usual dose of oral administration: is 3 to 4 divided doses a day leading to a total of about 30 to 120 mg per day; in intravenous injection, intramuscular injection and subcutaneous injection: about 15 mg/twice a day; inhalation of liquid aerosol: about 15 mg/2 ml, twice a day.

The concentration of ambroxol, the active agent, can vary when used for the methods of this disclosure and will depend on a variety of factors, including the type of composition or dosage form, the corresponding mode of administration, the nature and activity of the specific active agent, and the intended drug release profile.

The unit dose for administration by any administration method described herein will be in the range of from about 0.1 mg to about 10,000 mg, typically in the range of from about 0.1 mg to about 500 mg, from about 1 mg to 300 mg, from 10 to 150 mg. Dosages would be for an average 70 kg person and can be adjusted to suit a subject. The dosage for total administration per day may be between 0.1 to 1 mg; between 1 mg to 5 mg; between 5 mg to 10 mg; between 10 mg to 20 mg; between 20 mg to 30 mg; between 30 mg to 40 mg; between 40 mg to 50 mg; between 50 mg to 100 mg; between 100 mg to 150 mg; between 150 mg to 200 mg; between 200 mg to 300 mg; between 300 mg to 400 mg; between 400 mg to 500 mg; between 500 mg to 1000 mg; between 1000 mg to 1500 mg; between 1500 mg to 2000 mg; between 2000 mg to 2500 mg; between 2500 mg to 3000 mg; between 3000 mg to 4000 mg; between 4000 mg to 5000 mg; between 5000 mg to 7500 mg; between 7500 mg to 10,000 mg.

The pharmaceutical composition comprising ambroxol may be administered to a subject by any local or systemic route known in the art including enteral (e.g., oral, feeding tube, enema), topical (e.g., device such as a nebulizer for inhalation through the respiratory system, skin patch acting epicutaneously or transdermally, suppository acting in the rectum or vagina), and parenteral (e.g., subcutaneous, intravenous, intramuscular, intradermal, or intraperitoneal injection; buccal, sublingual, or transmucosal; inhalation or instillation intranasally or intratracheally). It will be appreciated that the preferred route may vary with the age, condition, gender, or health status of the subject; the nature of the disease or other pathological condition, including the number and severity of symptoms; and the chosen active ingredient.

Subject

As used herein, a "subject" and a "patient" has the same meaning and is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rodents, rabbits, guinea pigs, monkeys, etc.

Effective Amount: Therapeutically Effective Amount

The compositions are delivered in effective amounts. The term "effective amount" refers to the amount necessary or sufficient to realize a desired biologic effect which is, for example, at least one or more of reducing a symptom of a MPS III disease. The symptoms are described in this disclosure and, for example, would include reducing HS level in a subject, in a cell in a subject, in the urine of a subject, or increasing the fusion rate of autophagic vesicles in a cell in a subject. It is understood by those skilled in the art that the dosage amount will vary with the route and mode of administration, the rate of excretion, the duration of the treatment, the age, size, species of mammal (e.g., human patient), and other factors well known in the arts of medicine and veterinary medicine.

Effective dosage forms, modes of administration, and dosage amounts may be determined empirically, and making such determinations is within the skill of the art. It is understood by those skilled in the art that the dosage amount will vary with the route and mode of administration, the rate of excretion, the duration of the treatment, the age, size, species of mammal (e.g., human patient), and other factors well known in the arts of medicine and veterinary medicine.

Other Aspects

While this disclosure refers to ambroxol, it is understood that various forms of ambroxol, as "ambroxol" is used in this discussion, includes salts, solvates, and hydrates thereof, and including, for example, ambroxol hydrochloride.

Here, when stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity that a person skilled in the art would understand does not affect the operation of the invention or its patentability.

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect efficacy of the treatment) or "consisting of" (i.e., allowing only the elements listed in the claim other than impurities or inconsequential activities that are ordinarily associated with the invention) instead of the "comprising" term. Any of these three transitions can be used interchangeably to claim the invention.

Formulations for administration (i.e., pharmaceutical compositions) may include a pharmaceutically acceptable carrier and ambroxol. Pharmaceutically acceptable carriers may be, for example, aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents. In another aspect, a medicament (e.g., a pharmaceutical composition) containing ambroxol and one or more pharmaceutically acceptable excipients is provided. Further aspects will be apparent from the following description and claims, and any generalizations thereto.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

INCORPORATION BY REFERENCE

All patents, patent applications, and publications mentioned herein are hereby incorporated by reference in their entirety as if each individual publication was specifically and individually indicated to be incorporated by reference. In case of conflict, the present application, including any definitions herein, will control.

REFERENCES

1. Valstar, M. J., Ruijter, G. J., van Diggelen, O. P., Poorthuis, B. J., and Wijburg, F. A. (2008) Sanfilippo syndrome: a mini-review. Journal Of Inherited Metabolic Disease 31, 240-252
2. Meyer, A., Kossow, K., Gal, A., Muhlhausen, C., Ullrich, K., Braulke, T., and Muschol, N. (2007) Scoring evaluation of the natural course of mucopolysaccharidosis type IIIA (Sanfilippo syndrome type A). Pediatrics 120, e1255-1261
3. Boelens, J. J., Prasad, V. K., Tolar, J., Wynn, R. F., and Peters, C. (2010) Current international perspectives on hematopoietic stem cell transplantation for inherited metabolic disorders. Pediatric Clinics Of North America 57, 123-145
4. Ivanova, M. M., Changsila, E., Turgut, A., and Goker-Alpan, O. (2018) Individualized screening for chaperone activity in Gaucher disease using multiple patient derived primary cell lines. American Journal Of Translational Research 10, 3750-3761
5. Maegawa, G. H., Tropak, M. B., Buttner, J. D., Rigat, B. A., Fuller, M., Pandit, D., Tang, L., Kornhaber, G. J., Hamuro, Y., Clarke, J. T., and Mahuran, D. J. (2009) Identification and characterization of ambroxol as an enzyme enhancement agent for Gaucher disease. The Journal Of Biological Chemistry 284, 23502-23516
6. Narita, A., Shirai, K., Itamura, S., Matsuda, A., Ishihara, A., Matsushita, K., Fukuda, C., Kubota, N., Takayama, R., Shigematsu, H., Hayashi, A., Kumada, T., Yuge, K., Watanabe, Y., Kosugi, S., Nishida, H., Kimura, Y., Endo, Y., Higaki, K., Nanba, E., Nishimura, Y., Tamasaki, A., Togawa, M., Saito, Y., Maegaki, Y., Ohno, K., and Suzuki, Y. (2016) Ambroxol chaperone therapy for neuronopathic Gaucher disease: A Pilot Study. Annals Of Clinical And Translational Neurology 3, 200-215
7. Ambrosi, G., Ghezzi, C., Zangaglia, R., Levandis, G., Pacchetti, C., and Blandini, F. (2015) Ambroxol-induced rescue of defective glucocerebrosidase is associated with increased LIMP-2 and saposin C levels in GBA1 mutant Parkinson's disease cells. Neurobiology of Disease 82, 235-242
8. Bendikov-Bar, I., Maor, G., Filocamo, M., and Horowitz, M. (2013) Ambroxol as a pharmacological chaperone for mutant glucocerebrosidase. Blood Cells, Molecules & Diseases 50, 141-145
9. McNeill, A., Magalhaes, J., Shen, C., Chau, K. Y., Hughes, D., Mehta, A., Foltynie, T., Cooper, J. M., Abramov, A. Y., Gegg, M., and Schapira, A. H. (2014) Ambroxol improves lysosomal biochemistry in glucocerebrosidase mutation-linked Parkinson disease cells. Brain: A Journal Of Neurology 137, 1481-1495
10. Magalhaes, J., Gegg, M. E., Migdalska-Richards, A., and Schapira, A. H. (2018) Effects of ambroxol on the autophagy-lysosome pathway and mitochondria in primary cortical neurons. Scientific reports 8, 1385
11. Ivanova, M. M., Changsila, E., Iaonou, C., and Goker-Alpan, O. (2019) Impaired autophagic and mitochondrial functions are partially restored by ERT in Gaucher and Fabry diseases. PloS One 14, e0210617

EXAMPLES

Example 1 Positive Effect of Ambroxol on the Activity of Lysosomal Enzymes

Subjects:

Study included: 1) patients with MPS III Type A, 2) patients with MPS III Type B, 3) patients with MPS III Type C, 4) patients with MPS III Type D.

All blood samples are collected after obtaining informed consent according to an Internal Review Board (IRB).

Results:

Ambroxol increased NAGLU enzyme activity in MPS III Type B:

We show that ambroxol positively affected the cellular functions by improving enzyme activity, autophagy, and lysosomal function in an in vitro cell model derived from patients with mucopolysaccharidosis type III (MPS III).

We measured enzyme activity in PBMC (peripheral blood mononuclear cell) derived from MPS III Type B patients with NAGLU enzyme deficiency. After incubation for five days in the presence of 1, 10, and 100 µM of ambroxol, NAGLU enzyme activity was measured and compared negative control versus ambroxol incubated cells (FIG. 1). NAGLU enzyme activity was increased at 15% in ambroxol incubated cells with concentration 1 µM or 10 µM (FIG. 1). FIG. 1 shows the level of N-acetyl-alpha-glucosaminidase (NAGLU) enzyme activity in PBMC derived from a patient with MPS III Type B disease. PBMC were cultured for 5 days with an increasing concentration of ambroxol. Results are presented as a percentage of the negative control (i.e., cells cultured similarly but without incubation with ambroxol). Decreasing NAGLU activity in the presence of 100 μM of ambroxol was consistent with decreasing cell viability and inhibition of ATP production.

HGSNAT enzyme activity was measured and compared as negative control versus ambroxol incubated PBMC derived from a patient with MPS III Type C (FIG. 2). The enzyme assay demonstrated no increase in HGSNAT activity following ambroxol incubation in PBMC from a healthy subject (data not shown) and a patient with MPS III Type C.

Ambroxol activates and stabilizes autophagy-lysosome functions in MPS III.

Next, we demonstrate that ambroxol increases autophagy-lysosomal pathways independent from type of MPS III. To examine the effects of ambroxol on autophagy-lysosomal pathway, the autophagy dye DALGreen and lysosome marker LysoTracker Red were used.

MPS type III is a neurodegenerative lysosomal storage disorders whose symptoms are due to the incomplete lysosomal degradation of heparan sulfate. The degradative function of lysosomes also relies on the capacity of the lysosomal membranes to associate with target membranes, such as those of autophagic vacuoles. Interfering with the composition of lysosomal membranes has been shown to affect trafficking and fusion within the endolysosomal network.

Next, we showed the effects of ambroxol on autophagy-lysosome pathway cells derived from MPS III patients. The autophagy fusion was studied using autophagy detection reagent DALGreen. DALgreen fluorescence probe stained autophagosome on late-phase autophagy when autophagosome fused with a lysosome. Lysosome organelles were analyzed using LysoTracker Red DND-99 red-fluorescent dye which stained acidic organelles in live cells.

PBMC were isolated from the patient with MPS III-B disease, incubated five days with ambroxol, and then were stained. DALGreen staining revealed the increasing activity of autophagy fusion in ambroxol incubated in PBMC. LysoTracker Red staining showed a significant increasing proportion of acidic lysosomes in PBMC after ambroxol incubation. This experiment demonstrated that ambroxol significantly increases autophagy-lysosomal fusion in MPS III Type B cells (FIG. 3).

Macrophages derived from a patient with MPS III Type C. After 5 days incubation with ambroxol, PBMC were collected to measure enzyme activity (FIG. 2), and we used macrophages to study autophagy and lysosomal function (FIG. 4). DALGreen staining displayed aggregative density of green fluorescence signal, therefore increasing the activity of autophagy fusion in ambroxol incubated MPS III-C macrophages. LysoTracker Red staining showed a significant increasing proportion of acidic lysosomes in ambroxol incubated macrophages. This experiment confirmed that ambroxol significantly increases autophagy-lysosomal fusion in cells from patients with MPS III Type C.

Then, we studied autophagy fusion in PBMC derived from two patients with MPS III-D and a healthy control, who were incubated for five days with ambroxol (FIG. 5). DALGreen staining demonstrated a significant increase in autophagy fusion in ambroxol incubated healthy control and MPDSIII-D PBMC (FIG. 5).

These data are consistent with the observation obtained in MPS III-B PBMC.

SUMMARY

1. NAGLU enzyme activity was increased in ambroxol incubated PBMCs.
2. No change in HGSNAT activity following ambroxol incubation in healthy controls and MPS III-C PBMCs.
3. Ambroxol activates fusion of autophagic vesicles with lysosomes in cells (including PBMC and macrophages) derived from healthy controls, and MPS III-B, MPS III-C and MPS III-D patients.
4. Ambroxol activates lysosome function in cells derived from healthy controls, and cells derived from MPS III-B, MPS III-C and MPS III-D patients.

While this disclosure refers to ambroxol, it is understood that various forms of ambroxol are envisioned including salts, solvates, and hydrates thereof, and including, for example, ambroxol hydrochloride.

Example 2: Positive Effect of Ambroxol on the Activity of Lysosomal Enzymes

Measure Heparan Sulfate (HS) Level in Ambroxol Incubated PBMC:

MPS III is caused by the deficiency of enzymes involved in incomplete lysosomal degradation of heparin sulfate, and as a result, accumulation of heparin sulfate in cells.

Results: Ambroxol decreased heparan sulfate level in MPS III

To investigate the effect of ambroxol on HS degradation, the heparin sulfate ELISA assay (Aviva Systems Siology) was assessed. PBMC derived from healthy controls and MPS III patients were incubated with a concentration of ambroxol 1, 10 and 100 μM. PBMC after five days of incubation were collected and heparan sulfate levels were measured in cells extracts.

HS level decreased in ambroxol incubated PBMC derived from healthy controls. The results are shown in FIG. 6. In FIG. 6, the heparan sulfate (HS) level in PBMC derived from healthy controls (n=4). PBMC were cultured for 5 days with an increasing concentration of ambroxol. Results are presented as a percentage of the negative control (i.e., cells not cultured in the presence of ambroxol).

HS level was measured and compared as negative control versus ambroxol incubated PBMC derived from a patient with MPS III Type A (MPS III-A). ELISA assay demonstrated that HS level is decreased in MPS III-A cells. The results are shown in FIG. 7. In FIG. 7 the heparan sulfate (HS) level in PBMC derived from MPS III-A patient. PBMC were cultured for 5 days with an increasing concentration of ambroxol. Results are presented as a percentage of the negative control.

HS level was measured and compared as negative control (cells not incubated with ambroxol) versus ambroxol incubated PBMC derived from a patient with MPS III type B (MPS III-B). ELISA assay demonstrated that HS level is decreased in MPS III-B cell in the presence of 10 and 100 μM of ambroxol. The results are shown in FIG. 8. In FIG. 8, the heparan sulfate (HS) level in PBMC derived from the MPS III-B patient. PBMC were cultured for 5 days with an increasing concentration of ambroxol. Results are presented as a percentage of the negative control.

Level of HS was measured and compared as negative control versus ambroxol incubated PBMC derived from a patient with MPS III Type C (MPS III-C). Result demonstrated decreasing level of HS in cells after ambroxol incubation. The results are shown in FIG. 9. In FIG. 9, heparan sulfate (HS) level in PBMC derived from MPS III-C patient. PBMC were cultured for 5 days with an increasing concentration of ambroxol. Results are presented as a percentage of the negative control.

Also, we observed decreased HS level in MPS III Type D (MPS III-D) PBMC after incubation with 10 and 100 µM of ambroxol. The results are shown in FIG. 10. In FIG. 10, heparan sulfate (HS) level in PBMC derived from MPS III-D patient are shown. PBMC were cultured for 5 days with an increasing concentration of ambroxol. Results are presented as a percentage of the negative control.

We claim:

1. A method for treating a mucopolysaccharidosis type III (MPS III) disease in a subject, comprising
    administering to the subject a therapeutically effective amount of a composition comprising consisting essentially of ambroxol or a salt thereof as a pharmaceutically active agent that is effective for treating the MPS III disease without any other pharmaceutically active agent to the subject.

2. The method of claim 1, wherein the MPS III disease is at least one selected from the group consisting of:
    MPS III Type A;
    MPS III Type B;
    MPS III Type C;
    MPS III Type D; and
    MPS III Type E.

3. The method of claim 1, wherein the subject has a mutation in at least one gene selected from the group consisting of
    sulfamidase (SGSH) gene;
    N-acetyl-alpha-glucosaminidase (NAGLU) gene;
    acetyl-CoA: alpha-glucosaminide N-acetyltransferase (HGSNAT) gene;
    N-acetylglucosamine-6-sulfatase (GNS) gene; and
    arylsulfatase G (ARSG) gene.

4. The method of claim 1, wherein the subject has a reduced activity for at least one enzyme selected from the group consisting of:
    sulfamidase;
    N-acetyl-alpha-glucosaminidase;
    acetyl-CoA: alpha-glucosaminide N-acetyltransferase;
    N-acetylglucosamine-6-sulfatase; and
    arylsulfatase G.

5. The method of claim 1, wherein administering is at least one selected from the group consisting of:
    administering orally;
    administering transmucosally;
    administering sublingually;
    administering buccally;
    administering intranasally;
    administering transurethrally;
    administering rectally;
    administering topically;
    administering transdermally;
    administering parenterally; and
    administering intrathecally.

6. The method of claim 1, wherein the method increases enzymatic activity of N-acetyl-alpha-glucosaminidase (NAGLU) in the subject.

7. The method of claim 1, wherein the subject has a mutation in a gene encoding N-acetyl-alpha-glucosaminidase (NAGLU).

8. The method of claim 1, wherein the subject produces an N-acetyl-alpha-glucosaminidase with reduced activity and the method increases the activity of the N-acetyl-alpha-glucosaminidase.

9. The method of claim 1, wherein the amount of the composition is effective for increasing fusion rate of autophagic vesicles with lysosomes in a cell of the subject.

10. The method of claim 1, wherein the method decreases a level of heparan sulfate in the subject.

11. The method of claim 1, wherein the method increases intracellular heparan sulfate degradation in the subject.

12. The method of claim 1, wherein the method does not increase heparan-alpha-glucosaminide N-acetyltransferase (HGSNAT) activity in the subject.

13. The method of claim 1, wherein the ambroxol salt is ambroxol hydrochloride.

14. The method of claim 1 further comprising a step of diagnosing the MPS III disease in the subject before the administration of the composition to the subject.

15. The method of claim 14, wherein the diagnosing step is detecting reduced activity for at least one enzyme in the subject; wherein the enzyme is selected from the group consisting of:
    sulfamidase;
    N-acetyl-alpha-glucosaminidase;
    acetyl-CoA: alpha-glucosaminide N-acetyltransferase;
    N-acetylglucosamine-6-sulfatase; and
    arylsulfatase G.

16. The method of claim 14, wherein the diagnosing step is detecting mutation of at least one gene in the subject; wherein the gene is selected from the group consisting of:
    sulfamidase (SGSH) gene;
    N-acetyl-alpha-glucosaminidase (NAGLU) gene;
    acetyl-CoA: alpha-glucosaminide N-acetyltransferase (HGSNAT) gene;
    N-acetylglucosamine-6-sulfatase (GNS) gene; and
    arylsulfatase G (ARSG) gene.

* * * * *